US00PP18515P3

(12) United States Plant Patent
Lowry

(10) Patent No.: US PP18,515 P3
(45) Date of Patent: Feb. 26, 2008

(54) PEAR TREE, 'CAROLINA GOLD'

(50) Latin Name: *Pyrus communis*
Varietal Denomination: Carolina Gold

(75) Inventor: David Lowry, Phoenix, OR (US)

(73) Assignee: Associated Fruit Company, Phoenix, OR (US)

( * ) Notice: Subject to any disclaimer, the term of this patent is extended or adjusted under 35 U.S.C. 154(b) by 0 days.

(21) Appl. No.: 11/386,233

(22) Filed: Mar. 21, 2006

(65) Prior Publication Data

US 2007/0226857 P1 Sep. 27, 2007

(51) Int. Cl.
*A01H 5/00* (2006.01)

(52) U.S. Cl. ..... Plt./176

(58) Field of Classification Search ..... Plt./176
See application file for complete search history.

*Primary Examiner*—Kent Bell
(74) *Attorney, Agent, or Firm*—Wells St. John P.S.

(57) ABSTRACT

A new and distinct variety of pear tree *Pyrus communis* L and which is denominated varietally as 'Carolina Gold' and which produces a relatively large russetted colored pear which is mature for harvesting and shipment on or after August 29$^{th}$ under the ecological conditions prevailing near Phoenix, Oreg.

1 Drawing Sheet

BACKGROUND OF THE NEW VARIETY

The present invention relates to a new, novel and distinct variety of pear tree, *Pyrus communis,* and which has been denominated varietally as 'Carolina Gold,' hereinafter.

ORIGIN

The present variety of pear tree was discovered by the inventor within the cultivated region of his orchard, in 2003, as a chance, naturally occurring mutation of a 'Bartlett' pear tree (unpatented) that was then four years old. The particular tree upon which the naturally occurring mutation was found had previously been trained into a central leader system. The mutation occurred along the central axis of the tree at a point of about 90 cm. from the orchard floor. The mutation was identified during harvesting operations, and was marked for subsequent observation and repropagation thereafter.

ASEXUAL REPRODUCTION

The asexual reproduction of this new and distinct variety of pear tree was accomplished by grafting the mutation onto existing pear trees which were then four years. The existing pear trees had been grafted onto *Pyrus betulaefolia* pear rootstock (unnamed). This first asexual repropagation of the present variety was made in the same orchard of discovery which is located at 3721 Colver Road in Phoenix, Oreg. The fruit produced from this first asexual reproduction were subsequently examined and compared against the fruit produced from the originally discovered mutation. All the characteristics of the originally mutated tree and its fruit have been established and transmitted through this succeeding asexual propagation.

SUMMARY OF THE VARIETY

'Carolina Gold' is a new and distinct variety of pear tree which produces fruit which are considered equal to or larger than the fruit produced from the parent 'Bartlett' pear tree and which further has a russetted skin color which is quite distinctive relative to the fruit produced by the 'Bartlett' pear tree (unpatented) at full commercial maturity. In addition to the foregoing, the present variety holds well on the tree, and further the variety can be successfully harvested over a period of two or three weeks, if necessary. The present variety has a date of harvesting which is about 10 days, to as much as two weeks later than 'Bartlett' pear trees growing in the same geographical area, and under similar environmental conditions.

BRIEF DESCRIPTION OF THE DRAWINGS

The accompanying drawing which is provided is a color photograph of the new present variety. The photograph depicts two mature fruit both of which have been dissected substantially in the longitudinal plane and which reveals the flesh and the external coloration of the fruit is further shown. Additionally, the photograph displays a sample vegetative shoot bearing typical leaves. The colors in this photograph are as nearly true as is reasonably possible in a color representation of this type. Due to chemical development, processing and printing, the leaves and fruit depicted in these photographs may or may not be accurate when compared to the actual specimen. For this reason, future color references should be made to the color plates as provided in The Royal Horticultural Society Colour Chart 3$^{rd}$ Edition, and the descriptions as provided for hereinafter.

DETAILED DESCRIPTION

Referring more specifically to the pomological details of this new and distinct variety of pear tree, the following has been observed during the 2005 fruiting season under the ecological conditions prevailing at orchards which are located near Phoenix, Oreg. All major color code designations are by reference to the R.H.S. Colour Chart, 3$^{rd}$ Edition provided by The Royal Horticultural Society of Great Britain. Common color names are also occasionally used.

Tree:

*Vigor.*—Average to above average in vigor and considered somewhat more vigorous than the parent 'Bartlett' pear tree variety (unpatented). The tree as described herein was 6 years old at the time of this description (2005).

*Hardiness.*—The present variety is hardy when grown under the climatic conditions prevailing in the Medford pear-growing district of Oregon.

*Form.*—Generally speaking, it is upright to upright-spreading.

*Size.*—Height — 5.2 meters to about 5.5 meters.

*Size.*—Width — About 2.74 meters when grown in an orchard, and wherein the rows have a width of about 4.27 meters.

*Current season growth.*—About 38 cm. to as much as 114 cm. on vigorous current season shoots.

*Pruning.*—The present variety has been pruned annually into a central leader system and wherein a single trunk is maintained in a vertical position with smaller secondary limbs arising from the central leader.

*Productivity.*—Productive.

*Regularity of bearing.*—The tree bears fruit regularly year after year.

Trunk:

*Diameter.*—Considered average in size, and having a measurement of about 13 cm. to about 14 cm. when measured at a distance of about 20 cm. above ground level.

*Bark surface.*—Generally — Variable and considered roughened and slightly cracked with areas of light scarfskin. Remaining areas of the bark are relatively smooth.

*Bark color.*—Generally speaking, it is considered grey (Fan 4, Sheet 201-C).

*Bark lenticels.*—Numbers — Numerous and further exhibiting a flattened oval appearance.

*Bark lenticels.*—Surface Texture — Rough, calloused and slightly raised.

*Bark lenticels.*—Size — About 1 mm. to about 8 mm. in width; and about 1 to about 1.5 mm. in height.

*Bark lenticels.*—Color — Brown (Fan 4, Sheet 166-D).

Branches:

*Size.*—Average in size and diameter for the species. The largest branches arising from the central tree axis range in size from about 5 mm. to 6 cm. in diameter at their base.

*Surface texture.*—Similar to the trunk as described above. The surface texture is considered relatively smooth with light netting and scarfskin present.

*Branch lenticels.*—Numbers — Moderate.

*Branch color.*—Grey (Fan 4, Sheet 201-C).

*Lateral branches.*—Size — Ranging from 1 mm. to about 3.5 cm. in diameter at the base.

*Lateral branches.*—Color — The color of 2 year old and older lateral branches surfaces is grey (Fan 4, Sheet 201-D).

*2 year old lateral shoots.*—Surface Texture — Considered relatively smooth and having light scattered pubescence, or none at all.

*2 year old lateral wood.*—Lenticels — Present and variable in form from roughly oval to nearly diamond shaped in the vertical plane.

*Lenticels.*—Numbers — Numerous and variable in form.

*Lenticels.*—Size — About 1.5 mm. to about 3 mm. in width; and about 1.5 mm. to about 4.5 mm. in height.

*Lenticels.*—Surface Texture — Considered calloused.

*Lenticels.*—Surface Color — Calloused lenticels have a brownish color (Fan 4, Sheet 166-D).

*Color.*—Current Season Growth — Variable from Brown (Fan 4, Sheet 199-A), on more mature shoots; to a green color (Fan 3, Sheet 152-A) on less mature shoots.

*Current seasons shoots.*—Surface Texture — Relatively smooth with light pubescence and having numerous brown lenticels.

*Lenticels.*—Current Season Growth — The lenticels are roughly oval in form with a vertical measurement varying from about 1.5 mm. to about 3.5 mm. in height, and varying in width from about 1 mm. to about 2 mm.

*Current season shoots.*—Internode Length — Variable. However, most commonly from about 20 mm. to about 35 mm. between nodes.

*Spurs.*—Generally — Usually can be found along older lateral branches.

*Spurs.*—Size — About 4 mm. to about 6 mm. in diameter at their base, and about 10 mm. to as much as 50 mm. in length.

*Spurs.*—Internode Length — Variable and generally speaking within a range of about 2 mm. to about 6 mm. between the nodes.

*Spurs.*—Surface Texture — Considered similar to that of 2 year old and older lateral shoots. Spurs — Color — Brown (Fan 4, Sheet 201-D).

Leaves:

*Size.*—Generally considered medium for the species. Measurements of the present leaves have been taken from those leaves growing near mid-shoot on upright and vigorous current season shoots.

*Length.*—About 7.2 cm. to about 12.5 cm., including the leaf petiole.

*Width.*—About 4 cm. to about 6 cm.

*Thickness.*—Considered average for the species. That is neither unusually thick, nor unusually thin. This characteristic is not distinctive of the present variety.

*Surface texture.*—Upper Leaf Surface — Pubescent, however, the pubescence is widely scattered.

*Surface texture.*—Lower Leaf Surface — More pubescent relatively speaking than the upper surface.

*Surface texture.*—Moderately rugose, and more so in relative comparison to the leaves of the 'Bartlett' pear tree.

*Leaf glands.*—No leaf glands are present on the leaf.

*Leaf form.*—Generally — Variable, that is from ovate to broadly ovate, and less frequently approaching obovate.

*Leaf apices.*—Shape — Variable. Most frequently, these leaf apices are acute in form, but rounded and acuminate forms can also be found.

*Leaf base.*—Shape — Variable from rounded to moderately acute. The leaves are only moderately folded upwardly from the mid-rib.

*Leaf color.*—Upper Leaf Surface — Green (Fan 3, Sheet 137-B).

*Leaf color.*—Lower Leaf Surface — Light green (Fan 3, Sheet 138-C).

*Leaf vein coloration.*—Yellow-Green (Fan 3, Sheet 145-B). This color appears on both the upper and lower leaf surfaces.

*Leaf margin.*—Shape — Considered variable, but most frequently serrate in form with relatively large serrations. The serration apices are rather oblique.

*Leaf marginal form.*—Considered moderately undulate.

*Leaf petioles.*—Size — Generally considered average for the species.

*Leaf petioles.*—Length — Variable from 16 mm. to as much as 36 mm. in length.

*Leaf petioles.*—Thickness — About 1 mm. to about 2 mm. in thickness when measured at mid-petiole.

*Petiole color.*—Yellow-Green (Fan 3, Sheet 145-B), and having areas of darker green coloration along ridges which subtend the petiole groove (Fan 3, Sheet 144-B).

*Petiole surface texture.*—Lightly pubescent. The pubescence is finely scattered. Still further, the pubescence is more dense in and around the petiole groove.

*Leaf stipules.*—Numbers — Considered average in frequency and typically arising from the leaf petiole.

*Leaf stipules.*—Position — Typically found in a region which is about 1 mm. to about 8 mm. above the base of the petiole.

*Leaf stipules.*—Length — About 8 mm. to about 12 mm.

*Leaf petioles.*—Width — About 0.5 mm. to about 1 mm. in width when measured across the stipule base.

*Leaf stipules.*—Form — Considered linear lanceolate.

*Leaf stipules.*—Marginal form — The margins are considered serrate in shape. These serrations are relatively low and widely spaced.

*Leaf stipules.*—Color — Variable, most frequently a yellow-green (Fan 3, Sheet 145-C).

*Bloom timing.*—Date of first bloom for the new variety was Apr. 17, 2006. Date of full bloom was Apr. 23, 2006. Full bloom occurred from 2 to 3 days later for the 'Carolina Gold' in comparison with the parent 'Bartlett' pear trees at the same location. This date of bloom would be considered as midseason for the species.

*Flower size.*—Flower size is average for the species. Diameter of the flower ranges from 25 mm. to 34 mm. at full expansion. At times, the flower petals remain slightly cupped inwards at full maturity.

*Bloom quantity.*—The quantity of bloom produced by the tree is abundant. Bloom quantity is slightly less that the parent 'Bartlett'. The number of flowers produced from each floral bud is variable, but most frequently is 5.

The flower petals are medium in size, ranging from 13 mm. to 15 mm. in length and from 11 mm. to 13 mm. in width. Petal number is 5 per flower. Petal form is somewhat variable, most frequently slightly obovate by at times nearly oval. Petal color is white (Fan 4, Sheet 155-D). The petal claw is short and truncate in form. Claw width ranges from 1.5 mm. to 2.0 mm. at the base. Petal margins are variable, from smooth to moderately undulate. Petal apices are also variable, from uniformly rounded to occasionally notched or folded inwards.

*Flower pedicel.*—Size of the pedicel ranges from 12 mm. to 15 mm. in length and from 1.0 mm. to 2.0 mm in thickness at mid-pedicel. Pedicel color is green (Fan 3, Sheet 144-C). The pedicel surface is highly pubescent with moderately long individual hairs.

*Floral nectaries.*—The nectaries are dark yellow-green in color (Fan 3, Sheet 152-C).

*Flower calyx.*—The calyx surface is highly pubescent, with the hairs somewhat matted and downy in appearance. Calyx color is a bronze-green (Fan 3, Sheet 152-B).

*Flower sepals.*—The sepals are linear lanceolate in form with the apices somewhat reflexed downwards. The sepals range from 6 mm. to 8 mm. in length and from 2.5 mm. to 3.5 mm. in width across the base. The exterior (lower) surface of the sepals is lightly pubescent and light green in color (Fan 3, Sheet 145-B). The interior (upper) sepal surface is highly pubescent, with many relatively long and somewhat matted hairs. Color of the interior surface is a greenish-brown (Fan 3, Sheet 153-D).

*Anthers and pollen.*—Anther size is average, ranging from 1.0 mm. to 1.5 mm. in length and averaging 1.0 mm. in thickness. Anther color is purple-red (Fan 2, Sheet 60-C) both ventrally and dorsally. Pollen quantity is abundant. Pollen color is yellow (Fan 1, Sheet 8-C).

*Stamens.*—Stamen length ranges from 5 mm. to 7 mm. The stamen length varies somewhat from about equal to the height of the pistil to very slightly shorter than the pistil at full extension. Filament color is white (Fan 4, Sheet 155-C).

*Pistil.*—The pistil has five styles. Overall length varies from 6.5 mm. to 7.5 mm. The pistil surface is glabrous. Pistil color is a pale green (Fan 3, Sheet 145-C).

*Pollination.*—No controlled pollination studies have been done with the 'Carolina Gold' pear, so its pollination requirements are currently unknown. The original limb mutation is located within an orchard of standard 'Bartlett' pear trees and the original limb produces commercial volumes of fruit on a regular basis. The presence of seeds within the 'Carolina Gold' fruit at that location would seem to indicate the ability to cross-pollinate with the 'Bartlett' variety.

Fruit:

*Maturity when described.*—The fruit of the new variety is described at full commercial maturity.

*Date of harvesting.*—Aug. 29, 2005 under the ecological conditions prevailing at Phoenix, Oreg. This date of harvesting could be extended over a period of more than two weeks, if necessary, because the fruit holds well on the tree. During the 2004 harvesting season, fruit of the present variety was harvested during the first week of September. This date of harvesting is 10 days to as much as two weeks later than that of the Bartlett pear tree (unpatented) at the same geographical location.

*Size.*—Generally — Considered large for the species and equal to or slightly larger than the fruit produced by the 'Bartlett' pear tree (unpatented).

*Average diameter.*—About 68 mm. to about 77 mm.

*Average height.*—About 88 mm. to about 115 mm.

*Fruit form.*—Generally — Pyriform in its longitudinal aspect and having a moderate amount of variability in the length of the neck.

*Fruit form.*—Transverse Section — Considered globose with a slight amount of compression.

*Fruit uniformity.*—The fruit appears quite uniform and symmetrical throughout the tree.

*Fruit stem.*—Length — Variable from about 18 mm. to about 28 mm. Occasionally, stems over 30 mm. in length can be found.

*Stem.*—Thickness — 4.5 mm. to 7 mm. when measured at mid stem. The stem appears thicker at both ends, and has a diameter of about 6 mm. to about 8 mm.

*Stem.*—Shape — The stems are usually curved, with an attachment angle at the fruit neck varying from apical to oblique.

*Stem color.*—Brownish at commercial maturity, and having some greenish tones. (Fan 3, Sheet 152-A).

*Stem.*—Surface Texture — Glabrous.

*Stem.*—Lenticels — Numerous, small and irregularly shaped lenticels can be found.

*Lenticels.*—Size — About 0.5 mm. to about 1.5 mm. in diameter.

*Lenticels.*—Color — Light tan-brown (Fan 4, Sheet 165-C).

*Stem cavity.*—Shape — Globose and occasionally unevenly oval.

*Stem cavity.*—Width — Considered narrow. From about 5 mm. to about 8 mm. in diameter.

*Stem cavity.*—Depth — Considered shallow, about 3 mm. to about 4 mm.

*Stem cavity.*—Surface Texture — Ridging can appear within the stem cavity. Further, where the stem enters, the stem cavity is wide, and relatively obtuse.

*Stem cavity.*—Shoulders — Considered rounded.

*Fruit basin.*—Shape — Considered globose and moderately narrow and shallow.

*Fruit basin.*—Width — Variable from about 15 mm. to about 20 mm.

*Fruit basin.*—Depth — About 2 mm. to about 4 mm.

*Fruit basin.*—Shoulders — Rounded, and the basin sides vary from smooth to moderately undulate.

*Fruit basin.*—Surface Texture — Completely russetted and netted. Typically, concentric lines of netting encircle the calyx opening.

*Calyx sepals.*—Generally — Persistent, and are typically slight separated from each other from the basal attachment.

*Calyx opening.*—Shape — Variable from closed to partially open.

*Calyx tubes.*—Length — About 10 mm. to about 13 mm.

*Calyx tubes.*—Shape — Funnel shaped. As a general matter, stamen remnants are usually present within the calyx tube and are located in a marginal position.

*Core lines.*—Generally — Present. These core lines are distinct and clasping at the base of the calyx tube.

*Fruit core.*—Position — Considered distant from the stem end.

*Fruit carpels.*—Numbers — 5, and variable in form from obovate to oval. The fruit carpels often have a mucronate tip.

*Fruit carpels.*—Form — Considered closed and the inner surface of the carpel wall is considered smooth. Fruit carpel coloration. Not observed due to the rapid oxidation and color change which occurs in this area when the fruit is cut.

*Seeds.*—Numbers — Variable from 0 to 8. With full pollination, the fruit of the present variety has the potential of producing 10 seeds. Where no seeds are present within the fruit, the fruit has been set by parthenocarpy.

*Seeds.*—Shape — Plump. Although in some carpels, only shriveled seed coats were present. The seeds are ovate in form with an acute tip.

*Seeds.*—Shape — Ovate in form with an acute tip.

*Seeds.*—Length — About 6.5 mm. to about 8.5 mm.

*Seeds.*—Width — About 2.5 mm. to about 3.5 mm.

*Seeds.*—Color — At harvest time the seeds have a variable color from a light cream color (Fan 4, sheet 158-A); to a light brown (Fan 4, sheet 161-B). After the fruit has softened, the seeds darken to a dark brown (Fan 4, sheet 200-D).

*Fruit skin.*—Thickness — Considered relatively thick for the species, that is, the skin of the fruit has a thickness greater than the thickness of the skin in most fruit by *Pyrus communis,* and somewhat grainy in texture. The skin of the present variety is noticeably thicker than the fruit skin as found on the fruit produced by the 'Bartlett' pear tree (unpatented). This is not a distinguishing feature of the present variety.

*Fruit surface.*—Appearance — Completely russetted.

*Fruit skin adherence.*—The fruit skin adheres to the flesh at full commercial maturity.

*Fruit skin color.*—Progressing from a medium brown (Fan 4, sheet 199-A) when the fruit is first matured on the tree; but then lightening to an orange-brown (Fan 4, sheet 167-B) after the fruit is picked and begins to soften. No blush or ground color is visible on the fruit.

*Fruit skin lenticels.*—Numerous, small inconspicuous lenticels are present throughout the skin surface.

*Fruit skin lenticels.*—Shape — Variable in shape and having a generally globose form.

*Fruit skin lenticels.*—Color — Brown (Fan 4, sheet 168-C). Occasionally, a very light bloom can be detected on some fruit.

*Flesh color.*—White throughout the fruit (Fan 4, sheet 155-B).

*Flesh texture.*—Smooth and considered very juicy, and occasionally a few stone cells may be found. Those stone cells which are found are typically found in the fruit core area and along the core lines.

*Fruit flavor.*—Generally — Considered very good, and sweet, with a rich, somewhat spicy pear flavor. The fruit of the present variety is more acidic then the fruit produced by the 'Bartlett' pear tree (unpatented).

*Aroma.*—Generally — Sweet, distinct and pleasant.

*Fruit storage.*—The present variety hangs well on the tree and ripens evenly after harvest. Early indications of the present variety are that the storage ability is at least equal to that of the fruit produced by the Bartlett pear tree (unpatented).

Resistance to insects and disease: No particular susceptibilities were noted. The present variety has not been tested to expose or detect any susceptibilities or resistance to any known plant and/or fruit diseases.

Although the new variety of pear tree possesses the described characteristics when grown under the ecological conditions prevailing near Phoenix, Oreg., it should be understood that variations of the usual magnitude and characteristics incident to changes and growing conditions, fertilization, pruning, pest control and horticultural management are to be expected. The foregoing description does not constitute a commercial warranty. Consequently, this disclosure may not be relied upon that the present variety, when grown, under conditions other than Phoenix, Oreg. will display each of the characteristics as described in the present application. Therefore, the foregoing description may not be relied upon to support claims of breach of warranty or merchantability or fitness for any particular purpose which is directed to the present variety.

Having thus described and illustrated my new variety of pear tree, what I claim is new and desire to secure by Plant Letters Patent is:

1. A new and distinct variety of pear tree substantially as illustrated and described and which is characterized principally as to novelty by producing a russetted pear which is mature for harvesting and shipment approximately beginning on August $29^{th}$ to about September 14 under the ecological conditions prevailing in Phoenix, Oreg.

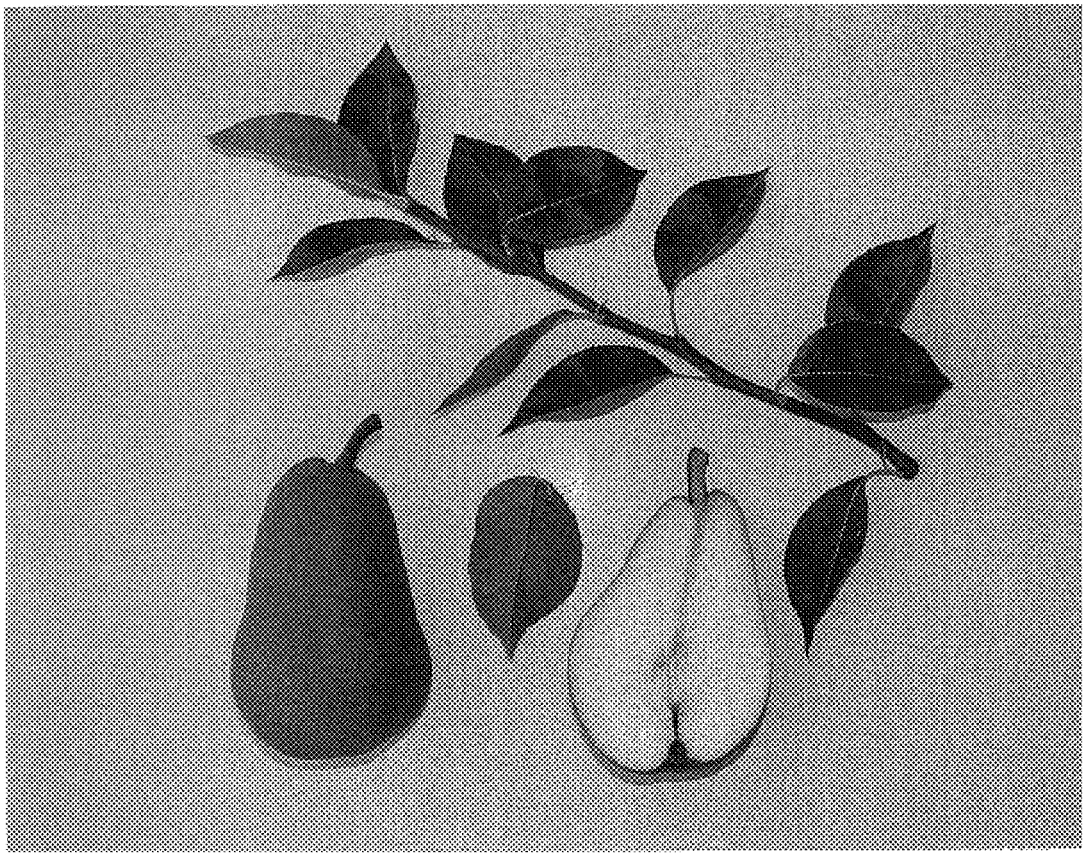

* * * * *